T864004

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED JULY 15, 1969

864 O.G. 729

769,561

PURIFICATION OF NEOCARBOXYLIC ACIDS

James A. Rigney, 159 N. River Road, Prince Edward Island, Charlottetown, Canada

Filed Oct. 22, 1968. Published July 15, 1969
Int. Cl. C07c *51/42, 53/22;* C07b *1/00*
U.S. Cl. 260—419
1 Sheet Drawing. 11 Pages Specification

$C_5$ to $C_{30}$ neo-acids are prepared substantially free of color-forming impurities from a crude neo-acid product obtained by the reaction of olefins with carbon monoxide and water in the presence of a boron trifluoride catalyst. The crude neo-acid products containing the color forming impurities are slurried with an insoluble hydrogenation catalyst, such as nickel, and reacted with hydrogen in a hydrogenation zone. The temperature in the hydrogenation zone is maintained from about 200° to 500° F. and hydrogen pressure ranges from about 100 to 1000 p.s.i.g. Thereafter, the hydrogenated product is separated from the insoluble hydrogenation catalyst and a substantially color stable neo-acid product is recovered.

T864004
July 15, 1969 J. A. RIGNEY DEF. PUB.
SN - 769561
PURIFICATION OF NEOCARBOXYLIC ACIDS
Filed Oct. 22, 1968
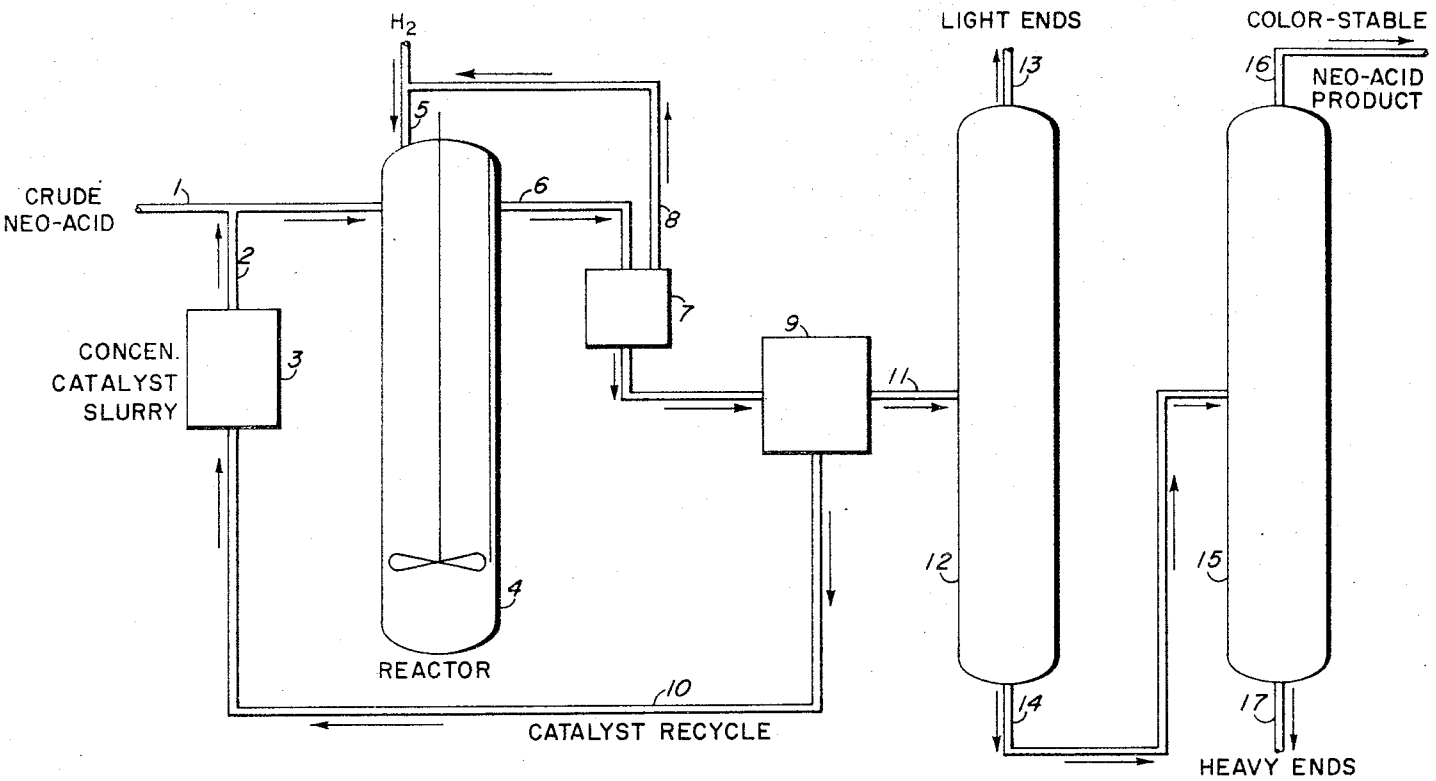
SLURRY HYDROGENATION OF NEO-ACIDS
J. A. Rigney Inventor
By Attorney